(12) United States Patent  
Foster

(10) Patent No.: US 8,954,168 B2
(45) Date of Patent: Feb. 10, 2015

(54) IMPLANTABLE DEVICE LEAD INCLUDING A DISTAL ELECTRODE ASSEMBLY WITH A COILED COMPONENT

(71) Applicant: Cardiac Pacemakers, Inc., St. Paul, MN (US)

(72) Inventor: Arthur J. Foster, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 13/800,159

(22) Filed: Mar. 13, 2013

(65) Prior Publication Data

US 2013/0325093 A1 Dec. 5, 2013

Related U.S. Application Data

(60) Provisional application No. 61/654,446, filed on Jun. 1, 2012.

(51) Int. Cl.
    *A61N 1/00* (2006.01)
    *A61N 1/05* (2006.01)
    *A61N 1/08* (2006.01)

(52) U.S. Cl.
    CPC .......... *A61N 1/059* (2013.01); *A61N 2001/086* (2013.01); *A61N 1/0573* (2013.01)
    USPC ...................................................... 607/119

(58) Field of Classification Search
    CPC ..... A61N 1/059; A61N 1/0565; A61N 1/056; A61N 1/057; A61N 1/0573; A61N 1/0587; A61N 1/36; A61N 1/04
    USPC ...................................................... 607/119
    See application file for complete search history.

(56) References Cited

U.S. PATENT DOCUMENTS 3,614,692 A  10/1971  Rozelle et al.
4,131,759 A  12/1978  Felkel
4,135,518 A   1/1979  Dutcher
(Continued)

FOREIGN PATENT DOCUMENTS

CN  1762510 A  4/2006
CN  1905789 A  1/2007
(Continued)

OTHER PUBLICATIONS

International Search Report and Written Opinion issued in PCT/US2013/065517, mailed Dec. 20, 2013, 11 pgs.
(Continued)

*Primary Examiner* — George Manuel
(74) *Attorney, Agent, or Firm* — Faegre Baker Daniels LLP

(57) ABSTRACT

A medical device lead includes an insulative body having a proximal region with a proximal end, and a distal region with a distal end. The medical device lead also includes a connector coupled to the proximal end of the insulative body of the lead to electrically and mechanically connect the lead to an implantable pulse generator. The medical device lead further includes a conductor extending through the insulative body with a proximal end electrically connected to the connector. A distal electrode assembly at a distal end of the insulative body includes a proximal portion electrically coupled to a distal end of the conductor, a distal portion, and an intermediate portion. The intermediate portion comprises a coiled element electrically connecting the proximal portion and distal portion.

20 Claims, 4 Drawing Sheets

(56) References Cited

U.S. PATENT DOCUMENTS

| | | | |
|---|---|---|---|
| 4,146,036 | A | 3/1979 | Dutcher et al. |
| 4,209,019 | A | 6/1980 | Dutcher et al. |
| 4,253,462 | A | 3/1981 | Dutcher et al. |
| 4,350,169 | A | 9/1982 | Dutcher et al. |
| 4,381,013 | A | 4/1983 | Dutcher |
| 4,404,125 | A | 9/1983 | Abolins et al. |
| 4,437,474 | A | 3/1984 | Peers-Trevarton |
| 4,484,586 | A | 11/1984 | McMickle et al. |
| 4,493,329 | A | 1/1985 | Crawford et al. |
| 4,574,800 | A * | 3/1986 | Peers-Trevarton ............ 606/1 |
| 4,643,202 | A | 2/1987 | Roche |
| 4,649,938 | A | 3/1987 | McArthur |
| 4,869,970 | A | 9/1989 | Gulla et al. |
| 5,002,067 | A | 3/1991 | Berthelsen et al. |
| 5,003,975 | A | 4/1991 | Hafelfinger et al. |
| 5,020,545 | A | 6/1991 | Soukup |
| 5,056,516 | A | 10/1991 | Spehr |
| 5,074,313 | A | 12/1991 | Dahl et al. |
| 5,144,960 | A * | 9/1992 | Mehra et al. .............. 607/125 |
| 5,201,865 | A | 4/1993 | Kuehn |
| 5,217,010 | A | 6/1993 | Tsitlik et al. |
| 5,222,506 | A | 6/1993 | Patrick et al. |
| 5,231,996 | A | 8/1993 | Bardy et al. |
| 5,241,957 | A | 9/1993 | Camp et al. |
| 5,243,911 | A | 9/1993 | Dow et al. |
| 5,246,014 | A | 9/1993 | Williams et al. |
| 5,259,395 | A | 11/1993 | Li |
| 5,300,108 | A | 4/1994 | Rebell et al. |
| 5,324,322 | A | 6/1994 | Grill, Jr. et al. |
| 5,330,522 | A | 7/1994 | Kreyenhagen |
| 5,354,327 | A | 10/1994 | Smits |
| 5,370,666 | A | 12/1994 | Lindberg et al. |
| 5,378,234 | A | 1/1995 | Hammerslag et al. |
| 5,387,199 | A | 2/1995 | Siman et al. |
| 5,417,208 | A | 5/1995 | Winkler |
| 5,425,755 | A | 6/1995 | Doan |
| 5,456,707 | A | 10/1995 | Giele |
| 5,476,485 | A | 12/1995 | Weinberg et al. |
| 5,483,022 | A | 1/1996 | Mar |
| 5,522,872 | A | 6/1996 | Hoff |
| 5,522,875 | A | 6/1996 | Gates et al. |
| 5,534,018 | A | 7/1996 | Wahlstrand et al. |
| 5,542,173 | A * | 8/1996 | Mar et al. .................... 29/825 |
| 5,545,205 | A | 8/1996 | Schulte et al. |
| 5,549,646 | A | 8/1996 | Katz et al. |
| 5,554,139 | A | 9/1996 | Okajima |
| 5,574,249 | A | 11/1996 | Lindsay |
| 5,584,873 | A | 12/1996 | Shoberg et al. |
| 5,599,576 | A | 2/1997 | Opolski |
| 5,609,622 | A | 3/1997 | Soukup et al. |
| 5,618,208 | A | 4/1997 | Crouse et al. |
| 5,727,552 | A | 3/1998 | Ryan |
| 5,727,553 | A | 3/1998 | Saad |
| 5,728,149 | A | 3/1998 | Laske et al. |
| 5,755,742 | A | 5/1998 | Schuelke et al. |
| 5,760,341 | A | 6/1998 | Laske et al. |
| 5,766,227 | A | 6/1998 | Nappholz et al. |
| 5,800,496 | A | 9/1998 | Swoyer et al. |
| 5,810,887 | A | 9/1998 | Accorti, Jr. et al. |
| 5,817,136 | A | 10/1998 | Nappholz et al. |
| 5,824,026 | A | 10/1998 | Diaz |
| 5,833,715 | A | 11/1998 | Vachon et al. |
| 5,849,031 | A | 12/1998 | Martinez et al. |
| 5,891,114 | A | 4/1999 | Chien et al. |
| 5,891,179 | A | 4/1999 | Er et al. |
| 5,935,159 | A | 8/1999 | Cross, Jr. et al. |
| 5,957,966 | A | 9/1999 | Schroeppel et al. |
| 5,957,970 | A | 9/1999 | Shoberg et al. |
| 5,968,087 | A | 10/1999 | Hess et al. |
| 6,016,447 | A | 1/2000 | Juran et al. |
| 6,057,031 | A | 5/2000 | Breme et al. |
| 6,078,840 | A | 6/2000 | Stokes |
| 6,083,216 | A | 7/2000 | Fischer, Sr. |
| 6,101,417 | A | 8/2000 | Vogel et al. |
| 6,106,522 | A | 8/2000 | Fleischman et al. |
| 6,141,593 | A | 10/2000 | Patag |
| 6,143,013 | A | 11/2000 | Samson et al. |
| 6,178,355 | B1 | 1/2001 | Williams et al. |
| 6,192,280 | B1 | 2/2001 | Sommer et al. |
| 6,208,881 | B1 | 3/2001 | Champeau |
| 6,249,708 | B1 | 6/2001 | Nelson et al. |
| 6,256,541 | B1 | 7/2001 | Heil et al. |
| 6,259,954 | B1 | 7/2001 | Conger et al. |
| 6,289,250 | B1 | 9/2001 | Tsuboi et al. |
| 6,295,476 | B1 | 9/2001 | Schaenzer |
| 6,304,784 | B1 | 10/2001 | Allee et al. |
| 6,317,633 | B1 | 11/2001 | Jorgenson et al. |
| 6,360,129 | B1 | 3/2002 | Ley et al. |
| 6,400,992 | B1 | 6/2002 | Borgersen et al. |
| 6,428,537 | B1 | 8/2002 | Swanson et al. |
| 6,434,430 | B2 | 8/2002 | Borgersen et al. |
| 6,456,888 | B1 | 9/2002 | Skinner et al. |
| 6,493,591 | B1 | 12/2002 | Stokes |
| 6,501,991 | B1 | 12/2002 | Honeck et al. |
| 6,501,994 | B1 | 12/2002 | Janke et al. |
| 6,510,345 | B1 | 1/2003 | Van Bentem |
| 6,516,230 | B2 | 2/2003 | Williams et al. |
| 6,526,321 | B1 | 2/2003 | Spehr |
| 6,564,107 | B1 | 5/2003 | Bodner et al. |
| 6,671,554 | B2 | 12/2003 | Gibson et al. |
| 6,701,191 | B2 | 3/2004 | Schell |
| 6,721,600 | B2 | 4/2004 | Jorgenson et al. |
| 6,721,604 | B1 | 4/2004 | Robinson et al. |
| 6,813,521 | B2 * | 11/2004 | Bischoff et al. ............ 607/122 |
| 6,850,803 | B1 | 2/2005 | Jimenez et al. |
| 6,854,994 | B2 | 2/2005 | Stein et al. |
| 6,866,044 | B2 | 3/2005 | Bardy et al. |
| 6,906,256 | B1 | 6/2005 | Wang |
| 6,920,361 | B2 | 7/2005 | Williams |
| 6,925,334 | B1 | 8/2005 | Salys |
| 6,944,489 | B2 | 9/2005 | Zeijlemaker et al. |
| 6,949,929 | B2 | 9/2005 | Gray et al. |
| 6,978,185 | B2 | 12/2005 | Osypka |
| 6,985,755 | B2 | 1/2006 | Cadieux et al. |
| 6,985,775 | B2 | 1/2006 | Reinke et al. |
| 6,993,373 | B2 | 1/2006 | Vrijheid et al. |
| 6,999,818 | B2 | 2/2006 | Stevenson et al. |
| 6,999,821 | B2 | 2/2006 | Jenney et al. |
| 7,013,180 | B2 | 3/2006 | Dublin et al. |
| 7,013,182 | B1 | 3/2006 | Krishnan |
| 7,047,075 | B2 | 5/2006 | Stubbs |
| 7,047,083 | B2 | 5/2006 | Gunderson et al. |
| 7,050,855 | B2 | 5/2006 | Zeijlemaker et al. |
| 7,113,827 | B2 | 9/2006 | Silvestri et al. |
| 7,123,013 | B2 | 10/2006 | Gray |
| 7,127,294 | B1 | 10/2006 | Wang et al. |
| 7,135,978 | B2 | 11/2006 | Gisselberg et al. |
| 7,138,582 | B2 | 11/2006 | Lessar et al. |
| 7,158,837 | B2 | 1/2007 | Osypka et al. |
| 7,174,219 | B2 | 2/2007 | Wahlstrand et al. |
| 7,174,220 | B1 | 2/2007 | Chitre et al. |
| 7,205,768 | B2 | 4/2007 | Schulz et al. |
| 7,239,916 | B2 | 7/2007 | Thompson et al. |
| 7,242,987 | B2 | 7/2007 | Holleman et al. |
| 7,257,449 | B2 | 8/2007 | Bodner |
| 7,289,851 | B2 | 10/2007 | Gunderson et al. |
| 7,363,090 | B2 | 4/2008 | Halperin et al. |
| 7,369,898 | B1 | 5/2008 | Kroll et al. |
| 7,378,931 | B2 | 5/2008 | Odahara et al. |
| 7,388,378 | B2 | 6/2008 | Gray et al. |
| 7,389,148 | B1 | 6/2008 | Morgan |
| 7,453,344 | B2 | 11/2008 | Maeda et al. |
| 7,535,363 | B2 | 5/2009 | Gisselberg et al. |
| 7,571,010 | B2 | 8/2009 | Zarembo et al. |
| 7,610,101 | B2 | 10/2009 | Wedan et al. |
| 7,630,761 | B2 | 12/2009 | Salo et al. |
| 7,689,291 | B2 | 3/2010 | Polkinghorne et al. |
| 7,765,005 | B2 | 7/2010 | Stevenson |
| 7,853,332 | B2 | 12/2010 | Olsen et al. |
| 7,877,150 | B2 | 1/2011 | Hoegh et al. |
| 7,912,552 | B2 | 3/2011 | Przybyszewski |
| 7,917,213 | B2 | 3/2011 | Bulkes et al. |
| 7,933,662 | B2 | 4/2011 | Marshall et al. |
| 7,953,499 | B2 | 5/2011 | Knapp et al. |

(56) References Cited

U.S. PATENT DOCUMENTS

| | | |
|---|---|---|
| 7,986,999 B2 | 7/2011 | Wedan et al. |
| 7,991,484 B1 | 8/2011 | Sengupta et al. |
| 8,000,801 B2 | 8/2011 | Stevenson et al. |
| 8,027,736 B2 | 9/2011 | Wahlstrand et al. |
| 8,032,230 B1 | 10/2011 | Cox et al. |
| 8,046,084 B2 | 10/2011 | Bodner |
| 8,099,177 B2 | 1/2012 | Dahlberg |
| 8,103,360 B2 | 1/2012 | Foster |
| 8,108,054 B2 | 1/2012 | Helland |
| 8,145,324 B1 | 3/2012 | Stevenson et al. |
| 8,170,688 B2 | 5/2012 | Wedan et al. |
| 8,200,342 B2 | 6/2012 | Stevenson et al. |
| 8,244,346 B2 | 8/2012 | Foster et al. |
| 8,255,055 B2 | 8/2012 | Ameri |
| 8,306,630 B2 | 11/2012 | Stubbs et al. |
| 8,332,050 B2 | 12/2012 | Perrey et al. |
| 8,335,572 B2 | 12/2012 | Ameri |
| 8,391,994 B2 | 3/2013 | Foster et al. |
| 8,401,671 B2 | 3/2013 | Wedan et al. |
| 8,543,209 B2 | 9/2013 | Tyers et al. |
| 8,666,508 B2 | 3/2014 | Foster et al. |
| 8,666,512 B2 | 3/2014 | Walker et al. |
| 8,670,840 B2 | 3/2014 | Wedan et al. |
| 8,676,344 B2 | 3/2014 | Desai et al. |
| 8,676,351 B2 | 3/2014 | Foster et al. |
| 8,688,236 B2 | 4/2014 | Foster |
| 2002/0065544 A1 | 5/2002 | Smits |
| 2002/0072769 A1 | 6/2002 | Silvian et al. |
| 2002/0111664 A1 | 8/2002 | Bartig et al. |
| 2002/0128689 A1 | 9/2002 | Connelly et al. |
| 2002/0144720 A1 | 10/2002 | Zahorik et al. |
| 2003/0028231 A1 | 2/2003 | Partridge et al. |
| 2003/0050680 A1 | 3/2003 | Gibson et al. |
| 2003/0083723 A1 | 5/2003 | Wilkinson et al. |
| 2003/0083726 A1 | 5/2003 | Zeijlemaker et al. |
| 2003/0092303 A1 | 5/2003 | Osypka |
| 2003/0093136 A1 | 5/2003 | Osypka et al. |
| 2003/0093138 A1 | 5/2003 | Osypka et al. |
| 2003/0139794 A1 | 7/2003 | Jenney et al. |
| 2003/0140931 A1 | 7/2003 | Zeijlemaker et al. |
| 2003/0144705 A1 | 7/2003 | Funke |
| 2003/0144716 A1 | 7/2003 | Reinke et al. |
| 2003/0144718 A1 | 7/2003 | Zeijlemaker |
| 2003/0144719 A1 | 7/2003 | Zeijlemaker |
| 2003/0144720 A1 | 7/2003 | Villaseca et al. |
| 2003/0144721 A1 | 7/2003 | Villaseca et al. |
| 2003/0204217 A1 | 10/2003 | Greatbatch |
| 2004/0014355 A1 | 1/2004 | Osypka et al. |
| 2004/0064161 A1 | 4/2004 | Gunderson et al. |
| 2004/0064173 A1 | 4/2004 | Hine et al. |
| 2004/0064174 A1 | 4/2004 | Belden |
| 2004/0088033 A1 | 5/2004 | Smits et al. |
| 2004/0097965 A1 | 5/2004 | Gardeski et al. |
| 2004/0122490 A1 | 6/2004 | Reinke et al. |
| 2004/0153049 A1 | 8/2004 | Hewitt et al. |
| 2004/0162600 A1 | 8/2004 | Williams |
| 2004/0167442 A1 | 8/2004 | Shireman et al. |
| 2004/0172117 A1 | 9/2004 | Hill et al. |
| 2004/0193140 A1 | 9/2004 | Griffin et al. |
| 2004/0243210 A1 | 12/2004 | Morgan et al. |
| 2004/0267107 A1 | 12/2004 | Lessar et al. |
| 2005/0070972 A1 | 3/2005 | Wahlstrand et al. |
| 2005/0090886 A1 | 4/2005 | MacDonald et al. |
| 2005/0113676 A1 | 5/2005 | Weiner et al. |
| 2005/0113873 A1 | 5/2005 | Weiner et al. |
| 2005/0113876 A1 | 5/2005 | Weiner et al. |
| 2005/0136385 A1 | 6/2005 | Mann et al. |
| 2005/0177135 A1 | 8/2005 | Hildebrand et al. |
| 2005/0182471 A1 | 8/2005 | Wang |
| 2005/0197677 A1 | 9/2005 | Stevenson |
| 2005/0222642 A1 | 10/2005 | Przybyszewski et al. |
| 2005/0222656 A1 | 10/2005 | Wahlstrand et al. |
| 2005/0222657 A1 | 10/2005 | Wahlstrand et al. |
| 2005/0222658 A1 | 10/2005 | Hoegh et al. |
| 2005/0222659 A1 | 10/2005 | Olsen et al. |
| 2005/0246007 A1 | 11/2005 | Sommer et al. |
| 2005/0267556 A1 | 12/2005 | Shuros et al. |
| 2005/0272280 A1 | 12/2005 | Osypka |
| 2005/0283167 A1 | 12/2005 | Gray |
| 2006/0009819 A1 | 1/2006 | Przybyszewski |
| 2006/0030774 A1 | 2/2006 | Gray et al. |
| 2006/0037461 A1 | 2/2006 | Yasumura |
| 2006/0041293 A1 | 2/2006 | Mehdizadeh et al. |
| 2006/0041294 A1 | 2/2006 | Gray |
| 2006/0041296 A1 | 2/2006 | Bauer et al. |
| 2006/0089691 A1 | 4/2006 | Kaplan et al. |
| 2006/0089695 A1 | 4/2006 | Bolea et al. |
| 2006/0089696 A1 | 4/2006 | Olsen et al. |
| 2006/0106442 A1 | 5/2006 | Richardson et al. |
| 2006/0118758 A1 | 6/2006 | Wang et al. |
| 2006/0129043 A1 | 6/2006 | Ben-Jacob et al. |
| 2006/0167536 A1 | 7/2006 | Nygren et al. |
| 2006/0200218 A1 | 9/2006 | Wahlstrand |
| 2006/0229693 A1 | 10/2006 | Bauer et al. |
| 2006/0247747 A1 | 11/2006 | Olsen et al. |
| 2006/0247748 A1 | 11/2006 | Wahlstrand et al. |
| 2006/0252314 A1 | 11/2006 | Atalar et al. |
| 2006/0253180 A1 | 11/2006 | Zarembo et al. |
| 2006/0271138 A1 | 11/2006 | MacDonald |
| 2006/0293737 A1 | 12/2006 | Krishman |
| 2007/0010702 A1 | 1/2007 | Wang et al. |
| 2007/0027532 A1 | 2/2007 | Wang et al. |
| 2007/0106332 A1 | 5/2007 | Denker et al. |
| 2007/0112398 A1 | 5/2007 | Stevenson et al. |
| 2007/0156205 A1 | 7/2007 | Larson et al. |
| 2007/0179577 A1 | 8/2007 | Marshall et al. |
| 2007/0179582 A1 | 8/2007 | Marshall et al. |
| 2007/0191914 A1 | 8/2007 | Stessman |
| 2007/0208383 A1 | 9/2007 | Williams |
| 2007/0255378 A1 | 11/2007 | Polkinghorne et al. |
| 2008/0009905 A1 | 1/2008 | Zeijlemaker |
| 2008/0033497 A1 | 2/2008 | Bulkes et al. |
| 2008/0039709 A1 | 2/2008 | Karmarkar |
| 2008/0049376 A1 | 2/2008 | Stevenson et al. |
| 2008/0051854 A1 | 2/2008 | Bulkes et al. |
| 2008/0057784 A1 | 3/2008 | Zarembo et al. |
| 2008/0058902 A1 | 3/2008 | Gray et al. |
| 2008/0119917 A1 | 5/2008 | Geistert |
| 2008/0125754 A1 | 5/2008 | Beer et al. |
| 2008/0129435 A1 | 6/2008 | Gray |
| 2008/0132985 A1 | 6/2008 | Wedan et al. |
| 2008/0132986 A1 | 6/2008 | Gray et al. |
| 2008/0140152 A1 | 6/2008 | Imran et al. |
| 2008/0154348 A1 | 6/2008 | Atalar et al. |
| 2008/0208290 A1 | 8/2008 | Phillips et al. |
| 2008/0243218 A1 | 10/2008 | Bottomley et al. |
| 2008/0262584 A1 | 10/2008 | Bottomley et al. |
| 2008/0269831 A1 | 10/2008 | Erickson |
| 2009/0005825 A1 | 1/2009 | MacDonald |
| 2009/0024180 A1 | 1/2009 | Kisker et al. |
| 2009/0024197 A1 | 1/2009 | Jensen |
| 2009/0099440 A1 | 4/2009 | Viohl |
| 2009/0099555 A1 | 4/2009 | Viohl et al. |
| 2009/0118610 A1 | 5/2009 | Karmarkar et al. |
| 2009/0149920 A1 | 6/2009 | Li et al. |
| 2009/0149933 A1 | 6/2009 | Ameri |
| 2009/0149934 A1 | 6/2009 | Ameri et al. |
| 2009/0198314 A1 | 8/2009 | Foster et al. |
| 2009/0204171 A1 | 8/2009 | Ameri |
| 2009/0210022 A1 | 8/2009 | Powers |
| 2009/0270948 A1 | 10/2009 | Nghiem et al. |
| 2009/0270956 A1 | 10/2009 | Vase et al. |
| 2009/0281608 A1 | 11/2009 | Foster |
| 2010/0010602 A1 | 1/2010 | Wedan et al. |
| 2010/0016935 A1 | 1/2010 | Strandberg et al. |
| 2010/0103215 A1 | 4/2010 | Iriguchi |
| 2010/0106215 A1 | 4/2010 | Stubbs et al. |
| 2010/0114277 A1 | 5/2010 | Zhao et al. |
| 2010/0125320 A1 | 5/2010 | Polkinghorne et al. |
| 2010/0137928 A1 | 6/2010 | Duncan et al. |
| 2010/0174348 A1 | 7/2010 | Bulkes et al. |
| 2010/0174349 A1 | 7/2010 | Stevenson et al. |
| 2010/0234929 A1 | 9/2010 | Scheuermann |
| 2010/0249892 A1 | 9/2010 | Bulkes et al. |

(56) References Cited

U.S. PATENT DOCUMENTS

| | | | |
|---|---|---|---|
| 2010/0292744 A1* | 11/2010 | Hill et al. | 607/2 |
| 2010/0331936 A1 | 12/2010 | Perrey et al. | |
| 2011/0060394 A1 | 3/2011 | Poore | |
| 2011/0079423 A1 | 4/2011 | Zhao et al. | |
| 2011/0087299 A1 | 4/2011 | Ameri | |
| 2011/0087302 A1 | 4/2011 | Ameri | |
| 2011/0093054 A1 | 4/2011 | Ameri | |
| 2011/0160805 A1 | 6/2011 | Erbstoeszer et al. | |
| 2011/0160816 A1 | 6/2011 | Stubbs et al. | |
| 2011/0160817 A1 | 6/2011 | Foster et al. | |
| 2011/0160818 A1 | 6/2011 | Struve | |
| 2011/0160828 A1 | 6/2011 | Foster et al. | |
| 2011/0160829 A1 | 6/2011 | Foster et al. | |
| 2011/0208280 A1 | 8/2011 | Li et al. | |
| 2011/0218422 A1 | 9/2011 | Atalar et al. | |
| 2011/0238146 A1 | 9/2011 | Wedan et al. | |
| 2011/0288403 A1 | 11/2011 | Kondabatni et al. | |
| 2012/0016451 A1 | 1/2012 | Struve et al. | |
| 2012/0022356 A1 | 1/2012 | Olsen et al. | |
| 2012/0035698 A1 | 2/2012 | Johnson et al. | |
| 2012/0053662 A1 | 3/2012 | Foster et al. | |
| 2012/0109270 A1 | 5/2012 | Foster | |
| 2012/0143273 A1 | 6/2012 | Stubbs et al. | |
| 2012/0161901 A1 | 6/2012 | Stevenson et al. | |
| 2012/0179233 A1 | 7/2012 | Wedan et al. | |
| 2012/0253340 A1 | 10/2012 | Stevenson et al. | |
| 2012/0271394 A1 | 10/2012 | Foster et al. | |
| 2013/0116764 A1* | 5/2013 | Walker et al. | 607/119 |
| 2013/0158641 A1 | 6/2013 | Foster et al. | |
| 2013/0190849 A1 | 7/2013 | Perrey et al. | |
| 2013/0190850 A1 | 7/2013 | Wedan et al. | |
| 2013/0282093 A1 | 10/2013 | Walker et al. | |
| 2014/0067030 A1 | 3/2014 | Walker et al. | |
| 2014/0155972 A1 | 6/2014 | Foster et al. | |

FOREIGN PATENT DOCUMENTS

| | | |
|---|---|---|
| CN | 101039619 A | 9/2007 |
| EP | 0897997 B1 | 2/2003 |
| EP | 1594564 A1 | 11/2005 |
| EP | 1852810 B1 | 11/2007 |
| JP | 2004141679 A | 5/2004 |
| JP | 2005501673 A | 1/2005 |
| JP | 2005515852 A | 6/2005 |
| JP | 2005515854 A | 6/2005 |
| WO | WO9606655 A1 | 3/1996 |
| WO | WO03063946 A2 | 8/2003 |
| WO | WO03063953 A2 | 8/2003 |
| WO | WO03089045 A2 | 10/2003 |
| WO | WO2004073791 A1 | 9/2004 |
| WO | WO2005030322 A1 | 4/2005 |
| WO | WO2006105066 A2 | 3/2006 |
| WO | WO2006093685 A1 | 9/2006 |
| WO | WO2007047966 A2 | 4/2007 |
| WO | WO2007089986 A1 | 8/2007 |
| WO | WO2007118194 A2 | 10/2007 |
| WO | WO2008051122 A1 | 5/2008 |
| WO | WO2009137186 A1 | 11/2009 |
| WO | WO2010078552 A1 | 7/2010 |

OTHER PUBLICATIONS

"High Voltage Engineering and Testing, 2nd Edition", edited by Hugh M. Ryan, Institution of Engineering and Technology, 2001, 15 pages.

Avalanche Breakdown, Wikipedia Article, captured Apr. 6, 2010, [http://en.wikipedia.org/wiki/Avalanche_breakdown].

Basso, Christophe, "SPICE Model Simulates Spark-Gap Arrestor", Electronics Design, Strategy, and News (EDN), Jul. 3, 1997, 4 pages.

Citel Inc., Data Sheet, BH Series 2 Electrode Miniature Gas Discharge Tube Surge Arrester—8mm, May 14, 2009, 2 pages.

File History for U.S. Appl. 11/015,807, filed Dec. 17, 2004 to Cooke, Daniel J. et al.

Gray, Robert W. et al., "Simple design changes to wires to substantially reduce MRI-induced heating at 1.5 T: implications for implanted leads", Magnetic Resonance Imaging 23 (2005) 887-891.

Hayes, David L., Chapter 4, "Generator and Lead Selection" from book entitled "Cardiac Pacing and Defibrillation A Clinical Approach", John Wiley & Sons, (c) 2000 Mayo Foundation, p. 129-157.

International Search Report and Written Opinion issued in PCT/US2008/085518 on Oct. 29, 2009, 15 pages.

International Search Report and Written Opinion issued in PCT/US2009/032838, mailed May 4, 2009, 14 pages.

International Search Report and Written Opinion issued in PCT/US2009/038629, mailed Jun. 29, 2009, 11 pages.

International Search Report and Written Opinion issued in PCT/US2009/056843, mailed Dec. 29, 2009, 13 pages.

International Search Report and Written Opinion issued in PCT/US2010/024062, mailed Sep. 27, 2010.

International Search Report and Written Opinion issued in PCT/US2010/033686 on Aug. 10, 2010, 12 pages.

International Search Report and Written Opinion issued in PCT/US2010/048620, mailed Apr. 5, 2011, 10 pages.

International Search Report and Written Opinion issued in PCT/US2010/053223, mailed Dec. 27, 2010, 11 pages.

International Search Report and Written Opinion issued in PCT/US2010/055130, mailed Mar. 10, 2011, 11 pages.

International Search Report and Written Opinion issued in PCT/US2010/055653, mailed Feb. 1, 2011, 14 pages.

International Search Report and Written Opinion issued in PCT/US2011/052541, dated Mar. 9, 2012, 22 pages.

International Search Report and Written Opinion issued in PCT/US2012/055673, mailed Dec. 13, 2012, 10 pages.

International Search Report and Written Opinion issued in PCT/US2013/037432, mailed Nov. 19, 2013, 17 pages.

International Search Report and Written Opinion issued in PCT/US2013/057732, mailed Dec. 13, 2013, 11 pages.

Invitation to Pay Additional Fees and Partial Search Report, dated Aug. 17, 2009, issued in PCT/US2008/085533, 6 pages.

Invitation to Pay Additional Fees and Partial Search Report, issued in PCT/US2010/024062, mailed May 7, 2010.

Partial International Search Report issued in PCT/US2011/052541, mailed Dec. 6, 2011, 4 pages.

Partial International Search Report issued in PCT/US2013/013432, mailed Jul. 17, 2013, 6 pages.

Partial International Search Report issued in PCT/US2013/037432, mailed Jul. 17, 2013, 6 pages.

Static Spark Gap Analysis, captured Dec. 24, 2002, [http://www.richieburnett.co.uk/static.html].

Third Party Submission Under 37 CFR 1.290 filed in U.S. Appl. No. 14/056,746 on May 20, 2014, 13 pages.

* cited by examiner

IMPLANTABLE DEVICE LEAD INCLUDING A DISTAL ELECTRODE ASSEMBLY WITH A COILED COMPONENT

CROSS-REFERENCE TO RELATED APPLICATION

This application claims priority to Provisional Application No. 61/654,446, filed Jun. 1, 2012, which is herein incorporated by reference in its entirety.

TECHNICAL FIELD

The present disclosure relates to implantable medical devices. More particularly, the present disclosure relates to a distal lead electrode assembly including a coiled electrode component and/or an electrically isolated moveable fixation helix.

BACKGROUND

Magnetic resonance imaging (MRI) is a non-invasive imaging procedure that utilizes nuclear magnetic resonance techniques to render images within a patient's body. Typically, MRI systems employ the use of a magnetic coil having a magnetic field strength of between about 0.2 to 3 Teslas (T). During the procedure, the body tissue is briefly exposed to radio frequency (RF) pulses of electromagnetic energy in a plane perpendicular to the magnetic field. The resultant electromagnetic energy from these pulses can be used to image the body tissue by measuring the relaxation properties of the excited atomic nuclei in the tissue.

During imaging, the electromagnetic radiation produced by the MRI system may be picked up by implantable device leads used in implantable medical devices such as pacemakers or cardiac defibrillators. This energy may be transferred through the lead to the electrode in contact with the tissue, which may lead to elevated temperatures at the point of contact. The degree of tissue heating is typically related to factors such as the length of the lead, the conductivity or impedance of the lead, and the surface area of the lead electrodes. Exposure to a magnetic field may also induce an undesired voltage on the lead. Further, in some cases, certain components of the lead can cause image artifacts in the magnetic resonance image.

SUMMARY

Disclosed herein are various embodiments of a medical device lead including a distal lead electrode assembly including a coiled electrode component, as well as medical device systems including such electrode assemblies.

In Example 1, a medical device lead includes an insulative body having a proximal region with a proximal end, and a distal region with a distal end. The medical device lead also includes a connector coupled to the proximal end of the insulative body of the lead to electrically and mechanically connect the lead to an implantable pulse generator. The medical device lead further includes a conductor extending through the insulative body with a proximal end electrically connected to the connector. A distal electrode assembly at a distal end of the insulative body includes a proximal portion electrically coupled to a distal end of the conductor, a distal portion, and an intermediate portion. The intermediate portion comprises a coiled element electrically connecting the proximal portion and distal portion.

In Example 2, the medical device lead according to Example 1, wherein the distal portion of the distal electrode assembly includes a contact electrode having an outer diameter larger than outer diameters of the proximal portion and intermediate portion, and wherein the insulative body extends over the distal electrode assembly to the contact electrode such that the contact electrode is exposed at the distal end of the medical device lead.

In Example 3, the medical device lead according to either Example 1 or 2, wherein the coiled element comprises a unifilar coil.

In Example 4, the medical device lead according to any of Examples 1-3, wherein a resistance of the coiled element is less than about 100 ohms.

In Example 5, the medical device lead according to any of Examples 1-4, and further comprising a fixation helix disposed within the distal electrode assembly and configured to extend from and retract into a distal end of the distal electrode assembly.

In Example 6, the medical device lead according to any of Examples 1-5, and further comprising an insulative layer configured to electrically isolate the fixation helix from the distal electrode assembly.

In Example 7, the medical device lead according to any of Examples 1-6, and further comprising a coupler disposed within the distal electrode assembly and fixedly attached to the fixation helix, wherein the coupler is rotatable with respect to the distal electrode assembly to translate the fixation helix longitudinally with respect to the distal electrode assembly.

In Example 8, the medical device lead according to any of Examples 1-7, wherein the coupler includes a slot configured to receive a distal end of an actuating device to rotate the coupler.

In Example 9, a distal electrode assembly for an implantable medical device includes a proximal portion configured for electrical connection to a conductive coil that delivers electrical energy to the distal electrode assembly, a distal portion including a contact electrode, and an intermediate portion comprising a coiled element electrically connecting the proximal portion to the distal portion.

In Example 10, the distal electrode assembly according to Example 9, wherein the coiled element comprises a unifilar coil.

In Example 11, the distal electrode assembly according to either Example 9 or 10, wherein the unifilar coil has a filar diameter of 0.002-0.007 inch (0.051-0.178 mm).

In Example 12, the distal electrode assembly according to any of Examples 9-11, wherein a resistance of the coiled element is less than about 100 ohms.

In Example 13, the distal electrode assembly according to any of Examples 9-12, and further comprising a fixation helix disposed within the distal electrode assembly and configured to extend from and retract into a distal end of the distal electrode assembly.

In Example 14, the distal electrode assembly according to any of Examples 9-13, and further comprising an insulative layer configured to electrically isolate the fixation helix from the distal electrode assembly.

In Example 15, a medical device lead includes an insulative body having a proximal region with a proximal end, and a distal region with a distal end. The medical device lead also includes a conductive coil extending through the insulative body, and a distal electrode assembly at a distal end of the insulative body. The distal electrode assembly includes a proximal portion electrically coupled to a distal end of the conductor, a distal portion, and an intermediate portion. The intermediate portion comprises a coiled element electrically connecting the proximal portion and distal portion. The coiled element comprises a unifilar coil having a pitch of less than two.

In Example 16, the medical device lead according to Example 15, and further comprising a fixation helix disposed within the distal electrode assembly and configured to extend from and retract into a distal end of the distal electrode assembly.

In Example 17, the medical device lead according to either Example 15 or 16, wherein the distal portion of the distal electrode assembly includes a contact electrode having an outer diameter larger than outer diameters of the proximal portion and intermediate portion, and wherein the insulative body extends over the distal electrode assembly to the contact electrode such that the contact electrode is exposed at the distal end of the medical device lead.

In Example 18, the medical device lead according to any of Examples 15-17, and further comprising a fixation helix disposed within the distal electrode assembly and configured to extend from and retract into a distal end of the distal electrode assembly.

In Example 19, the medical device lead according to any of Examples 15-18, and further comprising an insulative layer configured to electrically isolate the fixation helix from the distal electrode assembly.

In Example 20, the medical device lead according to any of Examples 15-19, and further comprising a coupler disposed within the distal electrode assembly and fixedly attached to the fixation helix, wherein the coupler is rotatable with respect to the distal electrode assembly to translate the fixation helix longitudinally with respect to the distal electrode assembly, and wherein the coupler includes a slot configured to receive a distal end of an actuating device to rotate the coupler.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
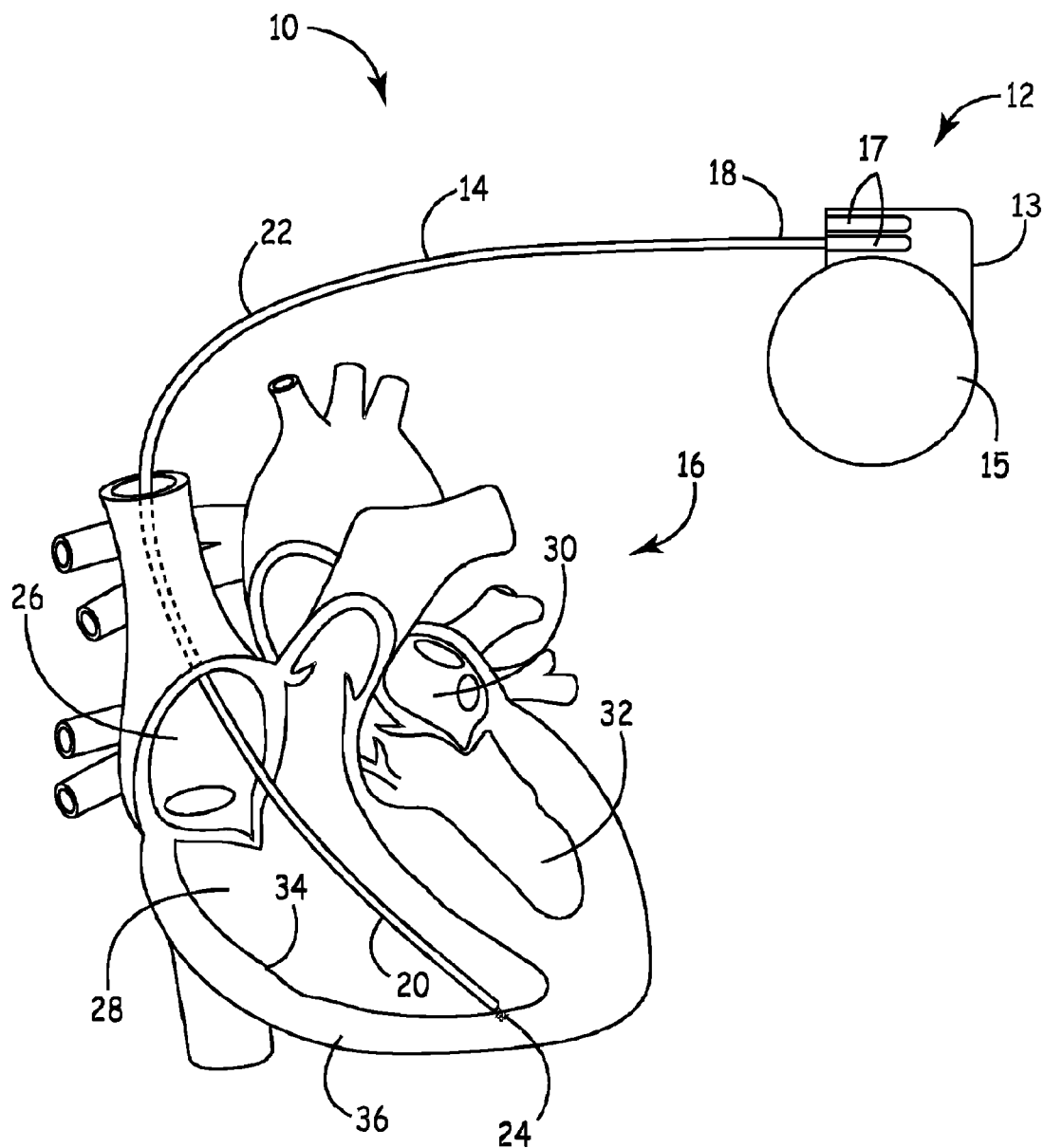
FIG. 1 is a combined cutaway of a heart and a perspective view of an implantable medical device and lead in accordance with one embodiment.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a perspective view of an implantable medical device (IMD) 10 in accordance with one embodiment. The IMD 10 includes a pulse generator 12 and a cardiac lead 14. The lead 14 operates to convey electrical signals between the heart 16 and the pulse generator 12. The lead 14 has a proximal region 18 and a distal region 20. The lead 14 includes a lead body, or flexible body 22, extending from the proximal region 18 to the distal region 20. The proximal region 18 is coupled to the pulse generator 12 and the distal region 20 is coupled to the heart 16. The distal region 20 includes an extendable/retractable fixation helix 24, which will be discussed in greater detail with respect to subsequent drawings, and which locates and/or secures the distal region 20 within the heart 16. In one alternative embodiment, the distal region 20 includes a plurality of tines or other structures for fixation of the lead 14 relative to the heart 20 (e.g., in a coronary vein or ventricular trabeculae).

The distal region 20 of the lead 14 has an axially compact design that accommodates a dedicated bipolar electrode configuration. The lead 14 may alternatively have other electrode configurations. As will be explained in further detail herein and shown in additional figures, the distal region 20 includes an electrically conductive electrode housing with a hollow interior that accommodates an extendible/retractable fixation helix 24. In some embodiments, the electrode housing includes a length having a coiled component that connects proximal and distal portions of the electrode housing. In some embodiments, the electrode housing is electrically isolated from the fixation helix 24, such as with an insulative layer between the electrode housing and fixation helix 24.

The pulse generator 12 typically includes a connector header 13 that couples the pulse generator 12 to the lead 14. The connector header 13 typically contains one or more bores 17 that is/are able to receive a connector (not shown) that is part of a connector assembly (not shown, but see 40 in FIG. 2, discussed herein) formed near the proximal region 18 of the lead 14, wherein electrical contacts (not shown) of the connector header 13 couple with lead contacts (not shown) of the connector assembly (not shown).

The connector header 13 can be attached to a hermetically sealed enclosure 15 that contains a battery, electronic circuitry, and other components known to those skilled in the art. Electrical contacts (not shown) in the connector header 13 can be a type known to those skilled in the art that are electrically connected via feedthroughs (not shown) mounted to extend through the hermetically sealed enclosure 15 in order to electrically couple the lead 14 with pulse generator 12.

The pulse generator 12 can be implanted subcutaneously within an implantation location or pocket in the patient's chest or abdomen. In embodiments in which the lead 14 is a neural lead, the pulse generator may alternatively be implanted at the patient's back or buttocks. The pulse generator 12 may be any implantable medical device known in the art or later developed, for delivering an electrical therapeutic stimulus to the patient. In various embodiments, the pulse generator 12 is a pacemaker, an implantable cardioverter/defibrillator (ICD), a cardiac resynchronization (CRT) device configured for bi-ventricular pacing, and/or includes combinations of pacing, CRT, and defibrillation capabilities.

The lead body 22 can be made from a flexible, biocompatible material suitable for lead construction. In various embodiments, the lead body 22 is made from a flexible, electrically insulative material. In one embodiment, the lead body 22 is made from silicone rubber. In another embodiment, the lead body 22 is made from polyurethane. In various embodiments, respective segments of the lead body 22 are made from different materials, so as to tailor the lead body 22 characteristics to its intended clinical and operating environments. In various embodiments, proximal and distal ends of the lead body 22 are made from different materials selected to provide desired functionalities.

The heart 16 includes a right atrium 26, a right ventricle 28, a left atrium 30 and a left ventricle 32. The heart 16 includes an endothelial inner lining or endocardium 34 covering the myocardium 36. In some embodiments as illustrated, the fixation helix 24, located at the distal region 20 of the lead, penetrates through the endocardium 34, and is imbedded within the myocardium 36. Alternatively, the lead 14 may be configured as a passive fixation lead as discussed herein. In one embodiment, the IMD 10 includes a plurality of leads 14. For example, it may include a first lead 14 adapted to convey electrical signals between the pulse generator 12 and the right ventricle 28, and a second lead (not shown) adapted to convey electrical signals between the pulse generator 12 and the right atrium 26. Additional leads may also be employed. For example, in various embodiments, a coronary venous lead (not shown) may be utilized for stimulating a left atrium 30 and/or a left ventricle 32 of the heart 16.

In the illustrated embodiment shown in FIG. 1, the fixation helix 24 penetrates the endocardium 34 of the right ventricle 28 and is imbedded in the myocardium 36 of the heart 16. In some embodiments, the fixation helix 24 is electrically active and thus can be used to sense the electrical activity of the heart 16 or to apply a stimulating pulse to the right ventricle 28. In other embodiments, the fixation helix 24 is not electrically active. In still other embodiments, the lead 14 is fixed relative to the heart 16 using passive structures (e.g., tines, spirals, etc.).

During operation, the lead 14 can be configured to convey electrical signals between the IMD 12 and the heart 16. For example, in those embodiments in which the IMD 12 is a pacemaker, the lead 14 can be utilized to deliver electrical stimuli for pacing the heart 16. In those embodiments in which the IMD 12 is an implantable cardiac defibrillator, the lead 14 can be utilized to deliver electric shocks to the heart 16 in response to an event such as a heart attack or arrhythmia. In some embodiments, the IMD 12 includes both pacing and defibrillation capabilities.

The electrical signals are carried between the IMD 12 and electrodes at the distal region 20 by one or more conductors extending through the lead 14. The one or more conductors are electrically coupled to a connector suitable for interfacing with the IMD 12 at the proximal region 18 of the lead 14 and to the one or more electrodes at the distal region 20. According to various embodiments, the one or more conductors include at least one composite conductor comprising a multiconductor wire. In some embodiments, the multiconductor wires are configured to deliver low voltage signals to the one or more electrodes.

Figure 2:
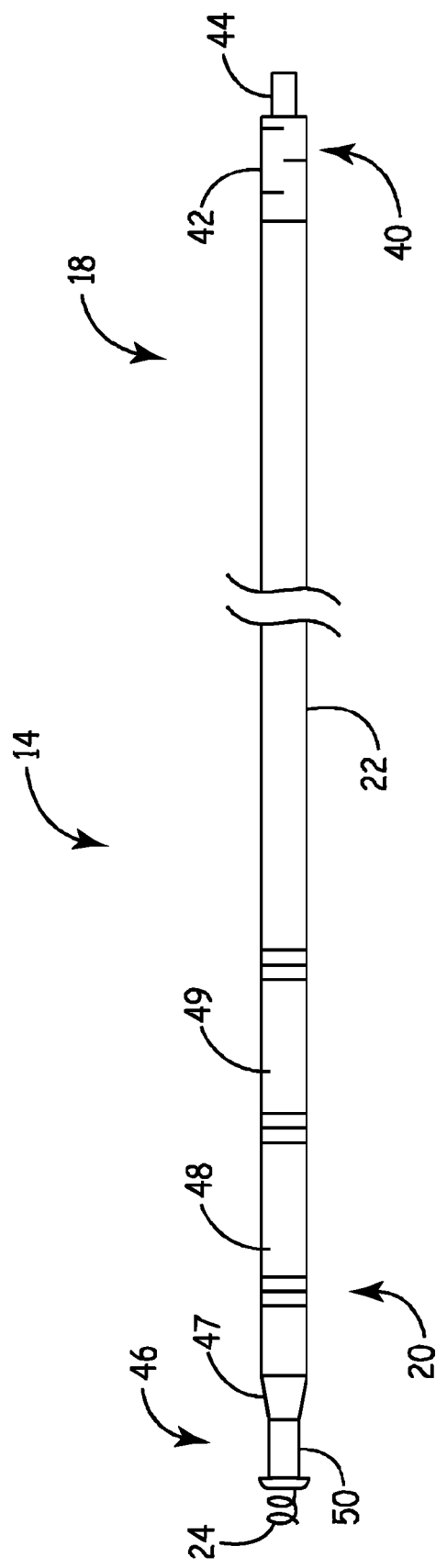
FIG. 2 is a side view of an embodiment of a lead as shown in FIG. 1.

FIG. 2 is an isometric illustration of a lead 14 according to some embodiments. A connector assembly 40 is disposed at or near the proximal region 18, or proximal end, of the lead 14. The connector assembly 40 includes a connector 42 and a terminal pin 44. The connector 42 is configured to be coupled to the lead body 22 and is configured to mechanically and electrically couple the lead 14 to the header 13 on the pulse generator 12 (see FIG. 1). In some embodiments, the terminal pin 44 includes an aperture (not shown) extending therethrough in order to accommodate a guide wire or an insertion stylet. For example, in some embodiments, a clinician may use a stylet inserted through the terminal pin 44 in the proximal region 40 to actuate the fixation helix 42 in the distal region 46. In alternative embodiments, the terminal pin 44 extends proximally from the connector 42 and in some embodiments is coupled to a conductor member (not visible in this view) that extends longitudinally through the lead body 22 such that rotating the terminal pin 44 relative to the lead body 22 causes the conductor member to rotate within the lead body 22.

A distal assembly 46 is disposed at or near the distal region 20 or distal end of the lead 14 or lead body 22. Depending on the functional requirements of the IMD 10 (see FIG. 1) and the therapeutic needs of a patient, the distal region 20 of the lead 14 may include one or more electrodes. In the illustrated embodiment, the distal region 20 includes one or more coil electrodes 48 and 49 that can function as shocking electrodes for providing, for example, a defibrillation shock to the heart 16. In some embodiments, the coil electrodes 48 and 49 include a coating that is configured to control (i.e., promote or discourage) tissue ingrowth. In various embodiments, the lead 14 may include only a single coil electrode. In various other embodiments, the lead 14 also includes one or more low-voltage electrodes (e.g., ring electrodes), such as electrode 47, along the lead body 22 in lieu of or in addition to the coil electrodes 48, 49. When present, the low-voltage electrodes operate as relatively low-voltage, pace/sense electrodes. As will be appreciated by those skilled in the art, a wide range of electrode combinations may be incorporated into the lead 14 within the scope of the various embodiments.

The distal assembly 46 includes a distal electrode assembly 50, within which the fixation helix 24, or helical electrode, is at least partially disposed. As will be explained in greater detail herein, the distal electrode assembly 50 accommodates a mechanism that enables the fixation helix 24 to move distally and proximally relative to the distal electrode assembly 50, but that includes structure (not seen in this view) that limits distal travel of the fixation helix 24 (relative to the distal electrode assembly 50) in order to reduce or prevent overextension of the fixation helix 24. In some embodiments, the distal end of the distal electrode assembly 50 is electrically active to provide electrical signals at the surface of the endocardial tissue. As noted herein, the fixation helix 24 operates as an anchoring means for anchoring the distal region 20 of the lead 14 within the heart 16. In alternative embodiments, the lead 14 is fixed relative to the heart 16 using passive structures (e.g., tines, spirals, etc.).

In some embodiments, the fixation helix 24, or helical electrode, is electrically active, and is used as a low-voltage, pace/sense electrode. In some embodiments, the fixation helix 24 is made of an electrically conductive material such as ELGILOY™, MP35N™, tungsten, tantalum, iridium, platinum, titanium, palladium, stainless steel as well as alloys of these materials. In alternative embodiments, the fixation helix 24 is electrically inactive and/or electrically isolated from the housing 50 with an insulative layer. For example, the fixation helix 24 could be made from a non-conductive material such as a polymer or ceramic.

The lead 14 is one exemplary implementation of a lead in accordance with the present disclosure, and other configurations for the lead 14 are also possible. For example, while coil electrodes 48, 49 are shown adjacent to each other, the coil electrode 49 may alternatively be disposed more proximally on the lead 14. As another example, the lead 14 may include a plurality of annular electrodes along the distal region 20 for providing pacing and/or sensing signals to adjacent tissue.

Figure 3A:
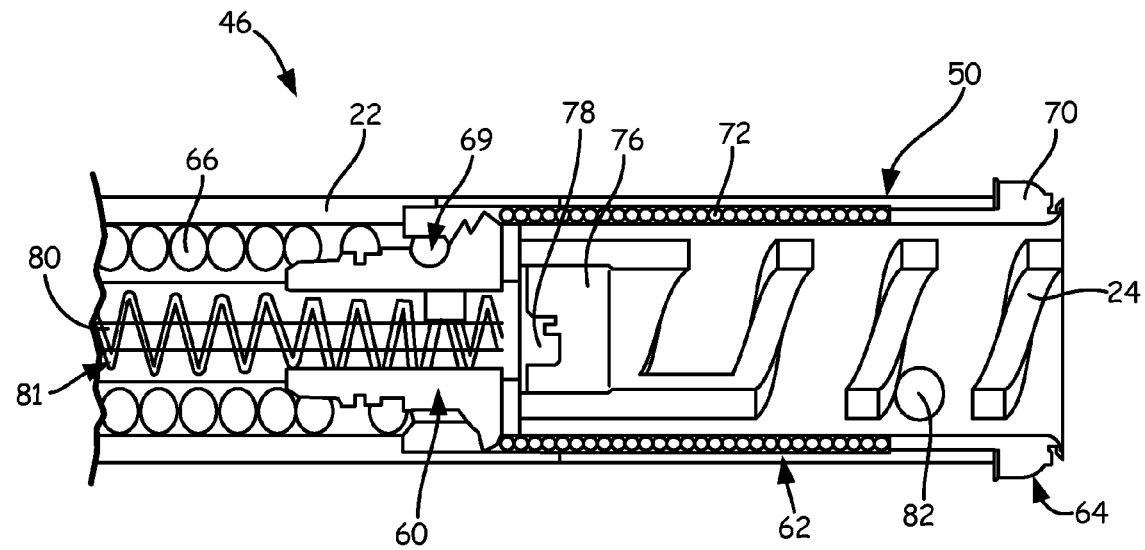
FIG. 3A is a sectioned side view of an embodiment of a distal end of a lead, including an electrode with a coiled portion.
Figure 3B:
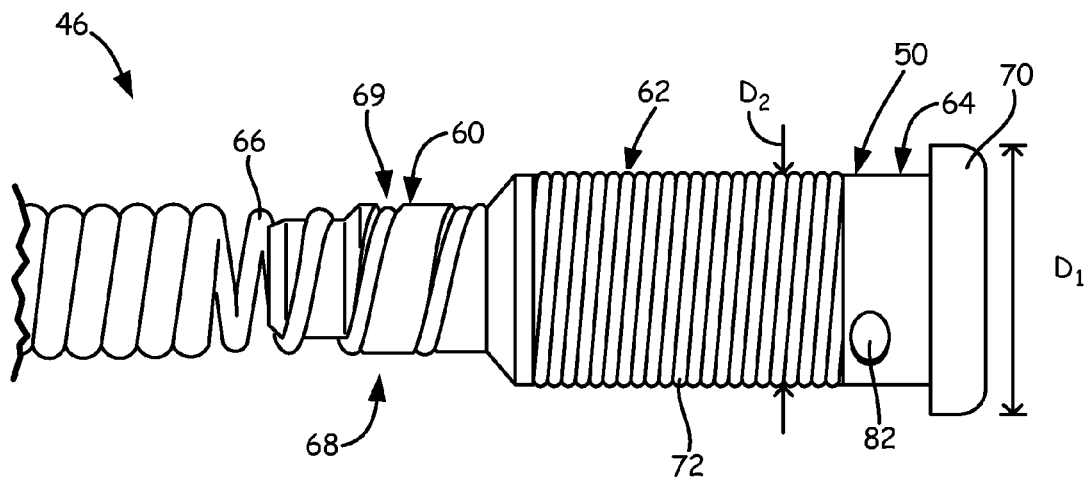
FIG. 3B is a side view of the distal end of the lead shown in FIG. 3A.

FIG. 3A is a sectioned side view, and FIG. 3B is a side view of an embodiment of the distal region 46 of the lead 14 including distal electrode assembly 50. In FIG. 3B, the lead body 22 is removed to better illustrate the features of the distal electrode assembly 50. The distal electrode assembly 50 includes a proximal portion 60, an intermediate portion 62, and a distal portion 64. The intermediate portion 62 mechanically and electrically couples the proximal portion 60 to the distal portion 64.

The proximal portion 60 is configured for coupling with a distal end of a coil conductor 66 extending through the lead body 22. In some embodiments, a proximal end of the coil conductor 66 (not shown) is connected to the connector assembly 40 at the proximal region 18 of the lead 14. In the embodiment shown, the coil conductor 66 couples with a conductor coupling region 68 of the proximal portion 60. For example, the proximal portion 60 may include a helical groove 69 that is sized and shaped to receive the distal end of the coil conductor 66, such that the coil conductor 66 is secured with respect to the proximal portion 60. The connection of the proximal portion 60 with the distal end of the coil conductor 66 thus electrically connects the electrode assembly 50 with the connector assembly 40. In some embodiments, the pitch of the coil conductor 66 is increased at the distal end of the coil conductor 66 to allow the coil conductor 66 to couple with the proximal portion 60. In some embodiments, the coil conductor 66 comprises one or more insulated filars that are stripped of insulation at the distal end of the coil conductor 66 to allow electrical contact between the coil conductor 66 and proximal portion 60.

The distal portion 64 is disposed at the distal end of the lead 14 and is electrically coupled to the proximal portion 60 via the intermediate portion 62. In some embodiments, the distal portion 64 includes a distal contact electrode 70 that has an outer diameter $D_1$ that is greater than the outer diameter $D_2$ of the proximal portion 60 and intermediate portion 62. The contact electrode 70 is configured to contact and deliver electrical energy to endocardial tissue when the lead 14 is implanted. In some embodiments, the lead body 22 extends over the proximal portion 60, intermediate portion 62, and parts of the distal portion 64 to the contact electrode 70. That is, the contact electrode 70 remains exposed in the assembled lead 14, while the remaining portions of the electrode assembly 50 are covered by the lead body 22.

The proximal portion 60 may be comprised of the same or similar material as the distal portion 64. The proximal portion 60 and distal portion 64 may include precious metals such as gold, silver, or platinum. Exemplary materials for the proximal portion 60 and distal portion 64 also include, but are not limited to, MPAg (MP35N with silver), MPTa (MP35N with tantalum), platinum-clad Ta, platinum-clad MP35N, MP35N, Nitinol, and palladium.

The intermediate portion 62 comprises a coiled element 72 that extends from the proximal portion 60 to the distal portion 64. The coiled element 72 includes one or more filars wound into a coil having an outer diameter substantially the same as adjacent sections of the proximal portion 60 and distal portion 64. As discussed herein, the coiled element 72 is electrically and mechanically connected to the proximal portion 60 and distal portion 64. In some embodiments, the coiled element 72 is connected to the proximal portion 60 and distal portion 64 by welding, swaging, or crimping the proximal and distal ends of the coiled element 72 to the proximal portion 60 and distal portion 64, respectively. In some embodiments, the coiled element 72 is covered (e.g., overmolded) with a polymeric material to improve the durability of the coiled element 72, provide suitable corrosion performance, and maintain the pitch and shape of the coiled element.

The coiled element 72 may have an outer diameter $D_2$ of less than about 0.1 inch (2.54 millimeter (mm)). For example, in some exemplary implementations, the outer diameter $D_2$ of the coiled element 72 is in the range of about 0.03 inch to about 0.1 inch (0.762-2.54 mm). In some embodiments, the coiled element 72 consists of a single filar of conductive material (i.e., unifilar) that is helically coiled with a plurality of co-radial turns. The turns of the coiled element 72 may be closely wound. For example, in some embodiments, the coiled element 72 has a pitch of between about one and two times the filar diameter. In the illustrated embodiment, the coiled element 72 has a pitch approximately equal to the filar diameter (i.e., the turns of the coiled element 72 abut each other). The pitch may be consistent along the length of the coiled element 72, or may be varied along at least a portion of the coiled element 72. One exemplary approach to incorporating variable pitch sections into the coiled element 72 is described in U.S. Patent App. Pub. No. 2009/0149933, entitled "Implantable Lead Having a Variable Coil Conductor Pitch," which is hereby incorporated by reference in its entirety. The direction of the pitch of the coiled element 72 may also be a function of the winding direction of other coiled elements (e.g., coil conductor 66). For example, in some embodiments, the coiled element 72 is wound in a direction opposite the coil conductor 66.

In some embodiments, the filar of the coiled element 72 has a diameter of between about 0.001 inch and 0.007 inch (0.025-0.178 mm). One exemplary material suitable for the coiled element 72 is MP35N including a silver core (e.g., 25% to 50% silver). Other exemplary materials suitable for the coiled element 72 include, but are not limited to, MPTa (MP35N with tantalum), platinum-clad Ta, platinum-clad MP35N, MP35N, Nitinol, and palladium. In some embodiments, the filar of the coiled element 72 is insulated. In some embodiments, the coiled element 72 is configured to have a resistance of less than about 100 ohms ($\Omega$).

The inclusion of a coiled element 72 in the electrode assembly 50 provides several advantages over solid electrode assemblies. For example, as discussed above, the proximal and distal portions 60, 64 may be comprised of precious metals. By using a coiled element 72 to connect the proximal portion 60 to the distal portion 64, less precious metal is used to fabricate the electrode assembly 50 versus an electrode assembly made of a solid length of material. Consequently, the overall cost to manufacture the lead 14 is reduced. At the same time, the coiled element 72 also generates fewer image artifacts in images generated using magnetic resonance imaging (MRI) while providing good radiopacity to discern the location of the electrode assembly 50 during imaging, since precious metals have a density that images well under the types of vision systems employed during implantation.

In addition, exposure of the lead 14 to MRI fields can result in localized heating of the contact electrode 70 due to excitation of the lead conductors (e.g., coil conductor 66). Conductors with high inductance (>1 pH) are more resistant to excitation in MRI fields. The inductance of the conductor is determined by its geometric properties, including whether the conductor is straight or coiled. For a coiled or wound conductor, such as the coiled element 72, several parameters influence its inductance, including the coil pitch, the outer diameter of the coiled element 72, the cross-sectional area of the coiled element 72, and the number of filars comprising the coiled element 72. For example, in some embodiments, the coil pitch (i.e., the distance between the centers of adjacent coil turns) may be small (e.g., one to two times the cable filar diameter). The coiled element 72 is shown having a pitch approximately equal to the filar diameter in FIGS. 3A and 3B (that is, turns of the coil are adjacent to each other). The pitch direction may also be selected (e.g., in the opposite direction as the coil conductor 66) to control heating of the electrode assembly 50 under MRI conditions. Thus, the dimensions and characteristics of the coil 52 may be selected to minimize the effects of magnetic resonance imaging (MRI) fields on the performance and response of the lead 14.

The fixation helix 24 may be disposed within a hollow interior of the electrode assembly 50. In some embodiments, the fixation helix 24 is a tube of conductive material laser cut or Swiss cut into a helical shape. A coupler 76 may be fixedly coupled to a proximal end of the fixation helix 24 to facilitate actuation of the fixation helix 24. In some embodiments, the coupler 76 may include a slot 78 that is accessible via an inner lumen 80 of the lead 14 with a stylet. For example, the stylet may be a bladed tip stylet having a distal feature sized and shaped to mate with the slot 78. To actuate the fixation helix 24, the stylet is pushed through the lumen 80 from the proximal region 18 of the lead 14 until the distal end of the stylet interfaces with the slot 78 in the coupler 76. The stylet is then rotated to rotate the fixation helix 24, which results in longitudinal movement of the fixation helix 24 relative to the lead 14. This allows the distal tip of the fixation helix 24 to be advanced into tissue during implantation, or retracted back into the electrode assembly 50.

In an alternative embodiment, the fixation helix 24 includes a torque tube 81 that is mechanically coupled to the fixation helix 24 (e.g., via the coupler 76). The torque tube 81 may be mechanically coupled to the terminal pin 44 on the connector assembly 40 to allow rotation and advancement of the fixation helix 24 by rotating the terminal pin 44. That is, the torque on the terminal pin 44 is transmitted to the fixation helix 24 via the torque tube 81. In some embodiments, the torque tube 81 is comprised of one or more polymeric fibers that are covered by an insulative coating or sheath. In some embodiments, the lumen 80 of the torque tube 81 comprises a smooth surface to facilitate insertion of a stylet or guide wire.

The electrode assembly 50 may also include a peg 82 against which turns of the fixation helix 24 rotate to maintain axial stability during actuation of the fixation helix 24. The peg 82 enables the fixation helix 24 to move distally and proximally relative to the electrode assembly 50, but limits distal travel of the fixation helix 24 (relative to the distal electrode assembly 50) in order to reduce or prevent over-extension of the fixation helix 24. The peg 82 may be made of a polymeric material, for example.

In alternative embodiments, the lead 14 may be fixated using passive fixation structures (e.g., tines) disposed on an exterior surface of the distal region 46, and/or a drug eluting element may be disposed in the hollow interior of the electrode assembly 50 in lieu of the fixation helix 24.

Figure 4A:
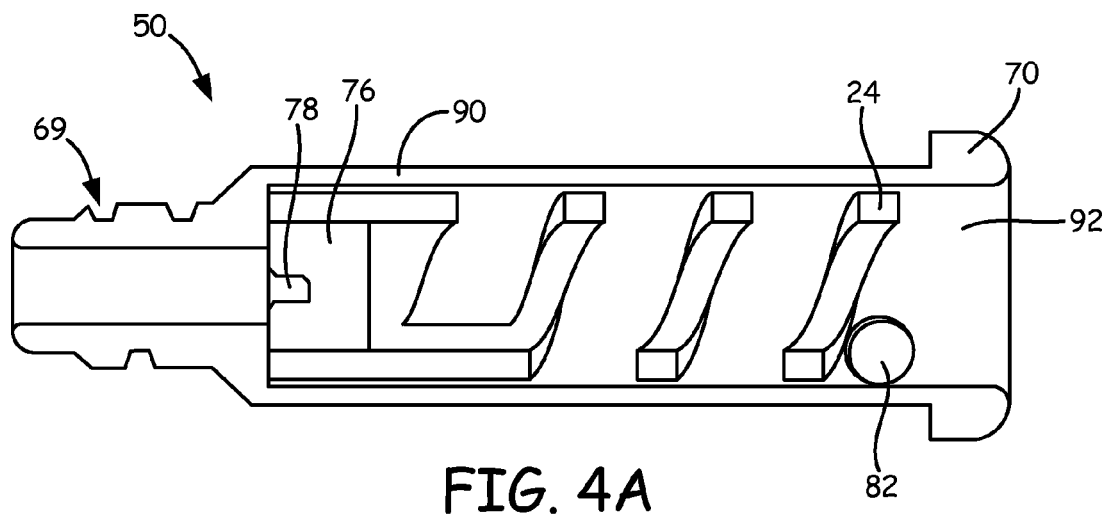
FIG. 4A is a sectioned side view of an embodiment of an electrode portion of a lead, including an insulative layer between the electrode housing and fixation helix.
Figure 4B:
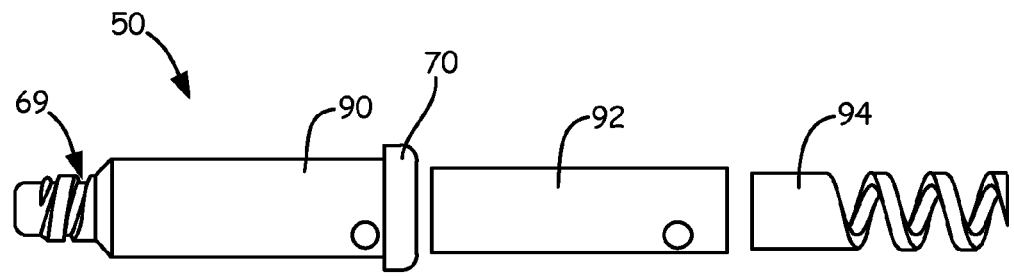
FIG. 4B is an exploded side view of the electrode portion shown in FIG. 4A.

FIG. 4A is a sectioned side view, and FIG. 4B is an exploded side view, of another embodiment of an electrode assembly 50 of the lead 14. The electrode assembly includes an outer conductive shell 90, an insulative layer 92, and a fixation helix 24. The electrode assembly 50 also includes a coupler 76 and a peg 82 having functionality similar to the embodiment illustrated in FIGS. 3A and 3B. The proximal end of the electrode assembly 50 also includes a helical groove 69 sized and shaped to couple with a conductive coil, similar to the embodiment illustrated in FIGS. 3A and 3B. Additionally, the conductive housing 90 includes a contact electrode 70 at the distal end of the conductive housing 90. In some embodiments, in the assembled lead 14 the lead body 22 is disposed over the portions of the conductive housing 90 up to the contact electrode 70, thereby leaving only the contact electrode 70 exposed at the distal end of the lead 14. While the electrode assembly 50 includes an outer conductive shell 90 comprised of a solid length of conductive material in the embodiment illustrated in FIGS. 4A and 4B, the electrode assembly 50 may alternatively be configured to include a coiled element 72 as described herein.

The insulative layer 92 is disposed between the outer conductive shell 90 and the fixation helix 24. In some embodiments, the insulative layer 92 electrically isolates the fixation helix 24 from the outer conductive shell 90. The insulative layer 92 may also be configured such that the fixation helix 24 is electrically inactive, and operates only as a fixation mechanism. The insulative layer 92 may be comprised of a material including, but not limited to, high durometer polyurethanes, hybrid high durometer polymers, ceramic, and epoxies, PEEK, ETFE, PTFE and derivatives, and/or parylene C. In some embodiments, the insulative layer 92 is formed on a metal substrate.

In this configuration, the tissue to be stimulated by the outer conductive shell 90 is distanced from the tissue attached to the fixation helix 24 for anchoring the lead 14. The tissue surrounding the fixation helix 24 may be agitated or going through the healing process and, as a result, may have a higher chronic threshold than other surrounding tissue. Consequently, by electrically isolating the fixation helix 24 from the outer conductive shell 90, the likelihood of electrical stimulation being delivered to tissue having a lower chronic threshold is increased.

The conductive housing 90 may be used in association with mapping systems to locate the distal region 46 of the lead 14 and/or facilitate development of a two- or three-dimensional representation of the heart 16 or one or more chambers of the heart 16. For example, the conductive housing 90 may be employed for establishing relative location and orientation of the lead 14 with respect to a mapping catheter located in another portion of the heart 16.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

I claim:

1. A medical device lead comprising:
   an insulative body having a proximal region with a proximal end, and a distal region with a distal end;
   a connector coupled to the proximal end of the insulative body of the lead configured to electrically and mechanically connect the lead to an implantable pulse generator;
   a conductor extending through the insulative body, a proximal end of the conductor electrically connected to the connector; and
   a distal electrode assembly at a distal end of the insulative body, the distal electrode assembly including a proximal portion that is mechanically and electrically coupled to a distal end of the conductor, a distal portion, an electrode at the distal portion, and an intermediate portion located between the proximal portion and the distal portion, wherein the distal end of the conductor terminates at the proximal portion of the distal electrode assembly, the intermediate portion is formed by a coiled element that terminates proximally with a first electrical connection at the proximal portion and distally with a second electrical connection at the distal portion to electrically connect the proximal portion to the distal portion, and the conductor is electrically connected to the electrode via the proximal portion, the intermediate portion, and the distal portion.

2. The medical device lead of claim 1, wherein the electrode comprises a contact electrode that is part of the distal portion of the distal electrode assembly, the contact electrode having an outer diameter larger than outer diameters of the proximal portion and intermediate portion, and wherein the insulative body extends over the distal electrode assembly to the contact electrode such that the contact electrode is exposed at the distal end of the medical device lead.

3. The medical device lead of claim 1, wherein the coiled element comprises a unifilar coil.

4. The medical device lead of claim 1, wherein a resistance of the coiled element is less than about 100 ohms.

5. The medical device lead of claim 1, and further comprising:
a fixation helix disposed within the distal electrode assembly and configured to extend from and retract into a distal end of the distal electrode assembly.

6. The medical device lead of claim 5, and further comprising:
an insulative layer configured to electrically isolate the fixation helix from the distal electrode assembly.

7. The medical device lead of claim 5, and further comprising:
a coupler disposed within the distal electrode assembly and fixedly attached to the fixation helix, wherein the coupler is rotatable with respect to the distal electrode assembly to translate the fixation helix longitudinally with respect to the distal electrode assembly.

8. The medical device lead of claim 7, wherein the coupler includes a slot configured to receive a distal end of an actuating device to rotate the coupler.

9. A distal electrode assembly for an implantable medical device, the distal electrode assembly comprising:
a proximal portion configured for electrical connection to a conductive coil that delivers electrical energy to the distal electrode assembly, the proximal portion having an outer diameter;
a distal portion including a contact electrode, the distal portion having an outer diameter; and
an intermediate portion electrically connecting the proximal portion to the distal portion, wherein the intermediate portion comprises a coiled element that terminates proximally at a first electrical connection at the proximal portion and distally with a second electrical connection at the distal portion to electrically connect the proximal portion to the distal portion, the coiled element having an outer diameter that is substantially the same as the outer diameters of the proximal portion and the distal portion.

10. The distal electrode assembly of claim 9, wherein the coiled element comprises a unifilar coil.

11. The distal electrode assembly of claim 10, wherein the unifilar coil has a filar diameter of 0.001-0.007 inch (0.025-0.178 mm).

12. The distal electrode assembly of claim 9, wherein a resistance of the coiled element is less than about 100 ohms.

13. The distal electrode assembly of claim 9, and further comprising:
a fixation helix disposed within the distal electrode assembly and configured to extend from and retract into a distal end of the distal electrode assembly.

14. The distal electrode assembly of claim 13, and further comprising:
an insulative layer configured to electrically isolate the fixation helix from the distal electrode assembly.

15. A medical device lead comprising:
an insulative body having a proximal region with a proximal end, and a distal region with a distal end;
a conductive coil extending through the insulative body; and
a distal electrode assembly at a distal end of the insulative body, the distal electrode assembly including an electrode, a proximal portion electrically and mechanically coupled to a distal end of the conductor, a distal portion supporting the electrode, and an intermediate portion, wherein the intermediate portion comprises a unifilar coil located between the proximal portion and the distal portion, the unifilar coil electrically connecting the proximal portion to the distal portion such that the conductive coil is electrically connected to the electrode, and wherein the unifilar coil has a coil winding pitch of less than two.

16. The medical device lead of claim 15, and further comprising:
a fixation helix disposed within the distal electrode assembly and configured to extend from and retract into a distal end of the distal electrode assembly.

17. The medical device lead of claim 16, wherein the electrode is a contact electrode having an outer diameter larger than outer diameters of the proximal portion and the intermediate portion, and wherein the insulative body extends over the distal electrode assembly to the contact electrode such that the contact electrode is exposed at the distal end of the medical device lead.

18. The medical device lead of claim 16, and further comprising:
a fixation helix disposed within the distal electrode assembly and configured to extend from and retract into a distal end of the distal electrode assembly.

19. The medical device lead of claim 18, and further comprising:
an insulative layer configured to electrically isolate the fixation helix from the distal electrode assembly.

20. The medical device lead of claim 19, and further comprising:
a coupler disposed within the distal electrode assembly and fixedly attached to the fixation helix, wherein the coupler is rotatable with respect to the distal electrode assembly to translate the fixation helix longitudinally with respect to the distal electrode assembly, and wherein the coupler includes a slot configured to receive a distal end of an actuating device to rotate the coupler.

* * * * *